(12) United States Patent
Goldstein et al.

(10) Patent No.: US 6,521,178 B1
(45) Date of Patent: *Feb. 18, 2003

(54) METHOD FOR SANITIZING MEDICAL EQUIPMENT USING MICROWAVES

(75) Inventors: Alan Scott Goldstein, Blue Ash, OH (US); Howard David Hutton, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/674,475

(22) PCT Filed: Apr. 30, 1999

(86) PCT No.: PCT/US99/09353

§ 371 (c)(1),
(2), (4) Date: Nov. 1, 2000

(87) PCT Pub. No.: WO99/56793

PCT Pub. Date: Nov. 11, 1999

(51) Int. Cl.[7] .................................................. A61L 2/00
(52) U.S. Cl. ............................. 422/21; 422/27; 422/28; 510/161; 510/372; 510/375
(58) Field of Search .............................. 422/21, 27, 28; 516/161, 372, 375

(56) References Cited

U.S. PATENT DOCUMENTS

| | | | | | |
|---|---|---|---|---|---|
| 4,055,505 A | * | 10/1977 | Gray | .......................... | 252/102 |
| 4,107,065 A | * | 8/1978 | Gray | .......................... | 252/99 |
| 4,110,242 A | * | 8/1978 | Hase et al. | .................. | 252/186 |
| 4,115,309 A | * | 9/1978 | Krause et al. | ............... | 252/186 |
| 4,314,036 A | * | 2/1982 | Throne et al. | ................. | 521/99 |
| 4,521,375 A | * | 6/1985 | Houlsby | ...................... | 422/29 |
| 5,201,411 A | | 4/1993 | Elkins et al. | | |
| 5,314,543 A | | 5/1994 | Elkins et al. | | |
| 5,552,112 A | | 9/1996 | Schiffmann et al. | | |
| 5,686,015 A | * | 11/1997 | Willey et al. | .......... | 252/186.39 |
| 6,039,921 A | | 3/2000 | Boucher | | |
| 6,287,346 B1 | | 9/2001 | Ofosu-Asante et al. | | |
| 6,306,219 B1 | | 10/2001 | Ofosu-Asante et al. | | |
| 6,322,748 B1 | | 11/2001 | Hutton et al. | | |

FOREIGN PATENT DOCUMENTS

| | | |
|---|---|---|
| WO | WO 98/03621 | 1/1998 |
| WO | WO 98/03622 | 1/1998 |
| WO | WO 98/03623 | 1/1998 |

* cited by examiner

*Primary Examiner*—Krisanne Thornton
(74) *Attorney, Agent, or Firm*—Jeffrey V. Bamber; Ken K. Patel

(57) ABSTRACT

A method by which medical equipment, such as surgical scalpels, can be sanitized using a detergent or treating composition containing a surfactant and a solvent such as water is disclosed. The method involves taking the used medical equipment and contacting it with the treating composition, and subjecting both the equipment and composition to microwaves. The composition foams during microwaving and/or immerses the equipment such that microwave arcing is avoided, and such that the medical equipment is sanitized.

18 Claims, No Drawings

METHOD FOR SANITIZING MEDICAL EQUIPMENT USING MICROWAVES

TECHNICAL FIELD

The invention generally relates to the field of cleaning compositions. More specifically, the invention relates to a method for cleaning, sanitizing and/or otherwise removing stains, odors, particulate matter and microbes from medical equipment surfaces by contacting the equipment with a cleaning composition and subjecting the equipment to microwaves. The composition is a liquid, gel, foam, or trigger-spray detergent composition. This method provides a convenient way in which medical equipment such that which is used in surgical operations can be sanitized on-site, for example at the hospital, in the operating room, or at a doctor's office. The detergent composition comprises water, surfactant, and optionally, a bleaching agent such as a peroxide in a liquid or gel formulation.

BACKGROUND OF THE INVENTION

Historically, doctors, surgeons, nurses and other medical personnel routinely use a variety of medical equipment to practice medicine on patients requiring an assortment of medical treatments. For example, surgical equipment including forceps, scalpels, bone chisels, drills and the like are used to perform medical operations on patients. In such cases, the equipment must be disinfected, and preferably sterilized, prior to use on a new patient. As used herein, the term "sanitize" broadly encompasses both disinfecting and sterilization, whereas disinfecting and sterilizing each refer to different levels of microbe removal as described in detail hereinafter. Quite often, equipment such as mirrors that are not particularly used to penetrate tissue, but nevertheless are contacted with tissue and the like when used during surgical operations or other medical procedures will therefore require disinfecting and/or sterilization prior to use on the next patient. Of the numerous pieces of medical equipment used, certain equipment such as scalpels, scalers, burs, and forceps, must be sterilized prior to re-use so as to prevent the transmission of disease from patient to patient.

Currently, doctors, surgeons, and other medical personnel employ either heat, cold or chemical vapor disinfection and sterilization techniques for which relatively expensive equipment is required in addition to time-consuming procedures using such equipment to disinfect and/or sterilize the medical equipment. By way of example, private doctors offices must employ personnel on overage of two to four hours per day just to disinfect and/or sterilize used medical equipment, and hospital require exponentially larger amounts of time. Moreover, governmental agencies in most countries require proper disinfection and/or sterilization of medical equipment, and doctors' offices and hospitals are routinely inspected for compliance with the agency's guidelines. In the U.S., for example, the Organizational Safety and Health Agency (OSHA), Public Health Service (CDC), and the American Medical Association (AMA) have relatively stringent guidelines on the sterilization/disinfection of medical equipment prior to use.

Unfortunately, conventional relatively inexpensive detergents used for washing tableware (i.e., glassware, china, silverware, plastic, etc.) or kitchenware in the home or institution are not particularly effective in obtaining disinfection, and particularly ineffective in obtaining sterilization of medical equipment. The particular requirements of cleansing tableware and leaving it in a sanitary, essentially stainless, residue-free state has indeed resulted in so many particular compositions that the body of art pertaining thereto is now recognized as quite distinct from other cleansing product art. Additionally, the body of art pertaining to fabric cleaning is immense and encompasses many formulations designed for stain removal, many including bleaches. However, medical offices and hospitals simply cannot effectively sterilize and/or disinfect their used medical equipment with such detergent compositions if used alone.

Accordingly, there is a need for method by which medical equipment can be efficiently and effectively disinfected and/or sterilized without the use of relatively expensive equipment and time-consuming techniques. There is also a need for such a method which can be conveniently employed in small private doctors' offices and the like.

SUMMARY OF THE INVENTION

The invention provides a method by which medical equipment, such as surgical scalpels, can be sanitized using detergent or treating composition containing a surfactant and a solvent such as water. The method involves placing used medical equipment in a non-metal container and contacting it with the treating composition, and subjecting both the equipment and composition to microwaves. The composition foams during microwaving and/or immerses the equipment such that microwave arcing is avoided, and such that the medical equipment is sanitized, preferably to the point of sterilization.

In accordance with one aspect of the invention, a method of sanitizing medical equipment containing microbes is provided. The method comprises the steps of: (a) contacting the medical equipment with an effective amount of a treating composition containing a surfactant and a solvent which generates heat under microwave radiation; (b) subjecting the medical equipment and the treating composition to microwaves for an effective amount of time such that a sanitizing amount of the microbes are removed from the medical equipment.

In accordance with another aspect of the invention, a medical equipment sanitizing product is provided. The medical equipment sanitizing product comprises a treating composition containing a surfactant and a solvent which generates heat under microwave radiation. The product further includes instructions for using of the treating composition comprising the steps of: (a) contacting the medical equipment with the treating composition; and (b) subjecting the medical equipment and treating composition to microwaves for an effective amount of time such that a sanitizing amount of microbes are removed from the medical equipment.

All percentages and proportions herein are by weight, and all references cited are hereby incorporated by reference, unless otherwise specifically indicated.

Accordingly, it is an advantage of the invention to provide a method by which medical equipment can be efficiently and effectively sanitized using an inexpensive treating composition. This and other features and attendant advantages of the present invention will become apparent to those skilled in the art from a reading of the following detailed description of the preferred embodiment and the appended claims.

DETAILED DESCRIPTION OF THE PREFERRED EMBODIMENT

The method of the invention essentially includes the steps of contacting microbe-containing medical equipment with a treating composition and subjecting both the composition and equipment to microwaves. Preferably, the treating composition contains a solvent which generates heat upon exposure to microwaves and is generally responsible for killing the microbes on the medical equipment. The treating composition preferably also contains a surfactant which aides in the sanitization of the equipment.

By "effective amount" of a treating composition, it is meant any amount capable of measurably removing microbes, tissue and other particulate matter from the surface of medical equipment. In general, this amount may vary quite widely, but typically will include from about 5 ml to about 20 ml per piece of medical equipment, but the amount must be sufficient to at least partially immerse the equipment to be sanitized. By "sanitizing amount", it is meant an amount of microbe removal which amounts to at least about 50% removal of the microbes on the dental equipment, more preferably at least about 90% removal, and most preferably at least about 99.9% removal of the microbes. As used herein, the term "disinfection" means removal of at least about 90% of the microbes, and the term "sterilization" means removal of at least about 99.9% of the microbes. The term "microbes" means any type of germ, bacteria, virus, parasite, including but not limited to, spore (e.g., *B. sutilis* or *C. sporogenes*), yeast (e.g., *C. albicans*), anaerobes (e.g., *P. gingivalis*), proteins/bugs (e.g., plaque), gram (+) (e.g., *S. mutans*), gram (−) (e.g., *E. coli*) and fungi (*A. meger*).

The treating composition is preferably a detergent composition which contains a surfactant, solvent, and optionally, also contains a bleaching agent. Preferably, the surfactant is present in an amount of from about 0.01% to about 50%, more preferably from about 1% to about 10%, and most preferably from about 2% to about 5% by weight. In preferred embodiments of the method invention, the treating composition further comprises an ingredient selected from the group consisting of clay, polycarboxylate thickeners, baking soda, carbonates, phosphates, hydrobenzoic acid, dicarboxylic acid, siloxanes, perfumes, bleach catalysts, and mixtures thereof. The treating composition can be in a variety of forms including a liquid, gel or granules.

The medical equipment is preferably placed in a nonmetal container into which the treating composition can be dispensed. It is important for the medical equipment to be totally immersed in the treating composition, or at least partially immersed such that the composition will be able to foam and substantially immerse the equipment with liquid and foam such that arcing does not occur during microwaving. A variety of containers can be used to help provide a place for the medical equipment to be placed and contacted with the treating composition. For example, a "boat-shaped" container having a false or grated bottom much like a broiling pan can be used such that the treating composition is placed in the false bottom and the equipment on top of the grating. Upon microwaving, the treating composition foams up from the grating so as to immerse the medical equipment to both sanitize the equipment and to prevent arcing. Other dispensing procedures can be used without departing from the scope of the invention so long as arcing is prevented during microwaving and such that a sanitizing amount of microbes are removed from the medical equipment.

The treating or detergent composition and dental equipment are subjected to microwaves for an effective amount of time to sanitize the equipment to a point that it is suitable for re-use on other patients. Typically an "effective amount of time" is from about 30 seconds to about 5 minutes, preferably from about 30 seconds to about 3 minutes, and most preferably from about 1 minute to 2 minutes. During this effective amount of time, the treating composition foams as described above and delivers the treating composition to substantially all exposed surfaces of the equipment. Optionally, the medical equipment can be rinsed with fresh solvent once it is removed from the microwave and allowed to dry. The drying time can be enhanced by placing the sanitized medical equipment into a conventional oven. Thereafter, the sanitized medical equipment is stored in a sanitary fashion (e.g. handling the sanitized medical equipment with rubber gloves and storing it in sealable plastic bags or the like) before use on the next patient.

Preferred aspects of the treating composition described herein include having the bleaching agent selected from the group consisting of diacyl peroxide, a source of hydrogen peroxide and bleach activator, a source of hydrogen peroxide, a chlorine bleach and mixtures thereof. Another highly preferred treating composition is a gel or liquid detergent composition comprising by weight: (a) from about 0.1% to about 60% of said bleaching agent which is selected from the group consisting of: i) diacyl peroxide having the general formula:

RC(O)OO(O)CR1

wherein R and R1 can be the same or different; ii) a source of hydrogen peroxide; iii) a source of hydrogen peroxide and a bleach activator; iv) a chlorine bleach; and v) mixtures thereof; (b) from 0% to about 95% of a solvent; (c) from 0.01% to about 50% of a surfactant; and (d) from 0% to about 7% of a thickener. Another highly preferred treating composition is a gel detergent composition comprising by weight: (a) from about 0.1% to about 10% of a diacyl peroxide having the general formula:

RC(O)OO(O)CR1

wherein R and R1 can be the same or different; (b) from 0.01% to about 50% of a surfactant; and (c) from 0% to about 7% of a thickener; the composition having a neat pH of from about 3 to about 10; and such that said diacyl peroxide remains undissolved in said composition.

Microwaves—By microwaving herein is meant exposing said surface treated with said compositions to microwave electromagnetic radiation. This is by any conventional means such as by placing the surface in a typical microwave such as used in homes and microwaving the surface for a sufficient time. Microwaves have an electromagnetic radiation wavelength of from about 1 cm to about 1 m, preferably from about 3 cm to about 30 cm, more preferably from about 11 cm to about 13 cm. See Aust. J. Chem., 1995, 48 [10], 1665–1692, Developments in Microwave-Assisted Organic Chemistry, by Strauss and Trainor.

Bleaching Agents

Suitable bleaching for use herein are listed below:

Diacyl Peroxide Bleaching Species—The composition of the present invention preferably contain diacyl peroxide of the general formula:

RC(O)OO(O)CR1

wherein R and R1 can be the same or different and are hydrocarbyls, preferably no more than one is a hydrocarbyl chain of longer than ten carbon atoms, more preferably at least one has an aromatic nucleus.

Examples of suitable diacyl peroxides are selected from the group consisting dibenzoyl peroxide, dianisoyl peroxide, benzoyl gluaryl peroxide, benzoyl succinyl peroxide, di-(2- methybenzoyl) peroxide, diphthaloyl peroxide, dinaphthoyl peroxide, substituted dinaphthoyl peroxide, and mixtures thereof, more preferably dibenzoyl peroxide, dicumyl peroxide, diphthaloyl peroxides and mixtures thereof. A particularly preferred diacyl peroxide is dibenzoyl peroxide.

Hydrogen Peroxide Source—The compositions of the present invention may comprise a source of oxygen bleach, preferably a source of hydrogen peroxide with or without a selected bleach activator. The source of hydrogen peroxide is typically any common hydrogen-peroxide releasing salt, such as sodium perborate or sodium percarbonate. Hydrogen peroxide sources are illustrated in detail in Kirk Othmer Review on Bleaching and include the various forms of sodium perborate and sodium percarbonate and modified forms. An "effective amount" of a source of hydrogen peroxide is any amount capable of measurably improving stain removal (especially of tea and tomato stains) from the soiled surface compared to a hydrogen peroxide source-free composition when the soiled surface is washed by the consumer.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxy-hydrate, urea peroxyhydrate, or sodium peroxide can be used herein. Sodium perborate monohydrate and sodium percarbonate are particularly preferred. Mixtures of any convenient hydrogen peroxide sources can also be used.

Another source of hydrogen peroxide is enzymes. Examples include Lipoxidase, glucose oxidase, peroxidase, alcohol oxidases, and mixtures thereof.

Bleach Activators—Numerous conventional bleach activators are known. See for example activators referenced hereinabove in the background as well as U.S. Pat. No. 4,915,854, issued Apr. 10, 1990 to Mao et al, and U.S. Pat. No. 4,412,934. Nonanoyloxybenzenesulfonate (NOBS) or acyl lactam activators may be used, and mixtures thereof with TAED can also be used. See also U.S. Pat. No. 4,634,551 for other typical conventional bleach activators. Also known are amido-derived bleach activators of the formulae: $R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. Further illustration of bleach activators of the above formulae include (6-octanamidocaproyl)oxybenzenesulfonate, (6-nonanamidocaproyl)-oxybenzenesulfonate, (6-decanamidocaproyl)oxybenzenesulfonate, and mixtures thereof as described in U.S. Pat. No. 4,634,551. Another class of bleach activators comprises the benzoxazin-type activators disclosed by Hodge et al in U.S. Pat. No. 4,966,723, issued Oct. 30, 1990. Still another class of bleach activators includes acyl lactam activators such as octanoyl caprolactam, 3,5,5-trimethylhexanoyl caprolactam, nonanoyl caprolactam, decanoyl caprolactam, undecenoyl caprolactam, octanoyl valerolactam, decanoyl valerolactam, undecenoyl valerolactam, nonanoyl valerolactam, 3,5,5-trimethyl-hexanoyl valerolactam, t-butylbenzoylcaprolactam, t-butylbenzoylvalerolactam and mixtures thereof. The present compositions can optionally comprise aryl benzoates, such as phenyl benzoate, and acety triethyl citrate.

Quaternary Substituted Bleach Activators—The present compositions can also comprise quaternary substituted bleach activators (QSBA). QSBA's herein typically have the formula $E-[Z]_n—C(O)-L$, wherein group E is referred to as the "head", group Z is referred to as the "spacer" (n is 0 or 1, i.e., this group may be present or absent, though its presence is generally preferred) and L is referred to as the "leaving group". These compounds generally contain at least one quaternary substituted nitrogen moiety, which can be contained in E, Z or L. More preferably, a single quaternary nitrogen is present and it is located in group E or group Z. In general, L is a leaving group, the pKa of the corresponding carbon acid (HL) of which can lie in the general range from about 5 to about 30, more preferably, from about 10 to about 20, depending upon the hydrophilicity of the QSBA. pKa's of leaving groups are further defined in U.S. Pat. No. 4,283,301.

Preferred QSBA's herein are water-soluble but have a tendency to partition to a definite extent into surfactant micelles, especially into micelles of nonionic surfactants.

Leaving groups and solubilizing tendencies of quaternary moieties which can be present in the QSBA's are further illustrated in U.S. Pat. No. 4,539,130, Sep. 3, 1985 incorporated by reference. This patent also illustrates QSBA's in which the quaternary moiety is present in the leaving group L.

British Pat. 1,382,594, published Feb. 5, 1975, discloses a class of QSBA's found suitable for use herein. In these compounds, Z is a poly(methylene) or oligo(methylene) moiety, i.e., the spacer is aliphatic, and the quaternary moiety is E. U.S. Pat. No. 4,818,426 issued Apr. 4., 1989 discloses another class of QSBA's suitable for use herein. These compounds are quaternary ammonium carbonate esters wherein, with reference to the above formula, the moiety Z is attached to E via a carbon atom but is attached to the carbonyl moiety through a linking oxygen atom. These compounds are thus quaternary ammonium carbonate esters. The homologous compounds wherein the linking oxygen atom is absent from Z are likewise known and are useful herein. See, for example, U.S. Pat. No. 5,093,022 issued Mar. 3, 1992 and U.S. Pat. No. 4,904,406, issued Feb. 27, 1990. Additionally, QSBA's are described in EP 552,812 Al published Jul. 28, 1993, and in EP 540,090 A2, published May 5, 1993.

Chlorine Bleach—Any chlorine bleach typically known in the art is suitable for use herein. Preferred chlorine bleaches for use herein include sodium hypochlorite, lithium hypochlorite, calcium hyposhlorite, chlorinated trisodium phosphates, and mixtures thereof. For more about chlorine bleaches see *Surfactant Science Series,* Vol. 5, Part II, pages 520–26.

Other Ingredients—Detersive ingredients or adjuncts optionally included in the instant compositions can include one or more materials for assisting or enhancing cleaning performance, treatment of the surface to be cleaned, or designed to improve the aesthetics or ease of manufacture of the compositions. Other adjuncts which can also be included in compositions of the invention at their conventional art-established levels, generally from 0% to about 20% of the composition, preferably at from about 0.1 % to about 10%, include one or more processing aids, color speckles, dyes, fillers, bleach-compatible enzymes, germicides, alkalinity sources, hydrotropes, stabilizers, perfumes, solubilizing agents, carriers. In general, materials used for the production of detergent compositions herein are preferably checked for compatibility with the essential ingredients used herein.

Exemplary germicides suitable for use include triclosan, triclocarbon, hydrogen peroxide and other oxygen bleaches, para-chloro-meta-xylenol, iodine/iodophors, selected alcohols, chlorohexidine, phenols, phospholipids, thymol, eugeniol, geraniol, oil of lemon grass, and limonene. Additionally, certain quaternary surfactants may also show antimicrobial action and may be included as an adjunct germicide.

In the preferred embodiments, additional ingredients such as water-soluble silicates (useful to provide alkalinity and assist in controlling corrosion), dispersant polymers (which modify and inhibit crystal growth of calcium and/or magnesium salts), chelants (which control transition metals), builders such as citrate (which help control calcium and/or magnesium and may assist buffering action), and alkalis (to adjust pH) are present. Additional bleach-improving materials such as bleach catalysts may be added.

Solvent—The solvent of the present invention is of the type in which the diacyl peroxide will dissolve. The preferred solvents are selected based upon the solubility parameter value of the diacyl peroxide employed. The solubility parameter value of a compound is available from literature sources such as Polymer Handbook. Values obtained by experiments are preferred. If the solubility parameter value is not available in the literature, the value can be calculated by using any of the methods described by Robert F. Fedor's article "A Method of Estimating Both the Solubility Parameters & Molar Volumes of Liquids", Polymer Engineering & Science, Feb. 1974, Vol 14, No. 2. Once the solubility parameter value is obtained of the diacyl peroxide, solvents are selected having a solubility parameter which fall within the diacyl peroxide solubility parameter.

Said solvent is preferably selected from the group consisting of N-alkyl pyrrolidones, such as N-ethyl pyrrolidone, diacetone alcohol, long chain (greater than $C_6$) alkyl ethers, cyclic alkyl ketones, and mixtures thereof. Amines, ethers and short chain (less than $C_6$) primary and secondary alcohols are preferably not present. Without being limited by theory, it is believed that the presence of these compounds may introduce stability problems. Thus, when diacyl peroxide and solvent are present in the compositions of this invention, it is further preferable that the amount of amine, ether, or primary or secondary alcohol be limited to no more than about 5%, preferably no more than about 3%, by weight of the composition.

Surfactants—Nonlimiting examples of surfactants useful herein include the conventional $C11-C_{18}$ alkyl benzene sulfonates ("LAS") and primary, branched-chain and random $C_{10}-C_{20}$ alkyl sulfates ("AS"), the $C_{10}-C_{18}$ secondary (2,3) alkyl sulfates of the formula $CH_3(CH_2)_x(CHOSO_3\text{-}M^+)$ $CH_3$ and $CH_3(CH_2)_y(CHOSO_3\text{-}M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}-C_{18}$ alkyl alkoxy sulfates ("AE$_x$S"; especially EO 1–7 ethoxy sulfates), $C_{10}-C_{18}$ alkyl alkoxy carboxylates (especially the EO 1–5 ethoxycarboxylates), the $C_{10}-C_{18}$ glycerol ethers, the $C_{10}-C_{18}$ alkyl polyglycosides and their corresponding sulfated polyglycosides, and $C_{12}-C_{18}$ alpha-sulfonated fatty acid esters.

If desired, the conventional nonionic and amphoteric surfactants such as the $C_{12}-C_{18}$ alkyl ethoxylates ("AE") including the so-called narrow peaked alkyl ethoxylates and $C_6-C_{12}$ alkyl phenol alkoxylates (especially ethoxylates and mixed ethoxy/propoxy), $C_{12}-C_{18}$ betaines and sulfobetaines ("sultaines"), and the like, can also be included in the overall compositions. The $C_{10}-C_{18}$ N-alkyl polyhydroxy fatty acid amides can also be used. Typical examples include the $C_{12}-C_{18}$ N-methylglucamides. See WO 9,206,154. Other sugar-derived surfactants include the N-alkoxy polyhydroxy fatty acid amides, such as $C_{10}-C_{18}$ N-(3-methoxypropyl) glucamide. The N-propyl through N-hexyl $C_{12}-C_{18}$ glucamides can be used for low sudsing. $C_{10}-C_{20}$ conventional soaps may also be used. If high sudsing is desired, the branched-chain $C_{10}-C_{16}$ soaps may be used. Mixtures of anionic and nonionic surfactants are especially useful. Other conventional useful surfactants are listed in standard texts.

Preferably, anionic surfactants are used herein. Without being limited by theory, it is believed that the use of anionic surfactants maximizes both cleaning performance and removal of residual bleach from the surface being treated.

One example of a group of surfactants suitable for use herein are those selected from the group consisting of alkyl ether sulfate, long chain (greater than about $C_7$) alkyl ethoxylate, linear alkyl benzene sulfonate (LAS), alkyl (ether) carboxylates, alkyl polyglucaside (APG), and mixtures thereof.

Thickeners—Thickeners for use herein can be selected from clay, polycarboxylates, such as Polygel®, gums, carboxymethyl cellulose, polyacrylates, and mixtures thereof. The preferred clay type herein has a double-layer structure. The clay may be naturally occurring, e.g., Bentonites, or artificially made, e.g., Laponite®. Laponite® is supplied by Southern Clay Products, Inc. See The *Chemistry and Physics of Clays*, Grimshaw, 4th ed., 1971, pages 138–155, Wiley-Interscience.

Bleach catalysts—If desired, detergent compositions herein may additionally incorporate a catalyst or accelerator to further improve bleaching or starchy soil removal. Any suitable bleach catalyst can be used. The compositions will comprise from about 0.0001% to about 0.1% by weight of bleach catalyst.

Typical bleach catalysts comprise a transition-metal complex, for example one wherein the metal coordinating ligands are quite resistant to labilization and which does not deposit metal oxides or hydroxides to any appreciable extent under the conditions of cleaning herein. Such catalyst compounds often have features of naturally occurring compounds such as enzymes but are principally provided synthetically. Highly preferred accelerators include, for example, the cobalt 3+catalysts, especially $\{Co(NH_3)_5Cl\}^{2+}$ or equivalents thereof with various alternate donor ligands. Such complexes include those formerly disclosed for use in laundry compositions in U.S. Pat. No. 4,810,410 to Diakun et al, issued Mar. 7, 1989. The active species thereof is believed to be $\{Co(NH_3)_5(OOH)\}^{2+}$ and is disclosed in J. Chem. Soc. Faraday Trans., 1994, Vol. 90, 1105–1114. Alternate catalysts or accelerators are the noncobalt transition metal complexes disclosed in this reference, especially those based on Mo(VI), Ti(IV), W(VI), V(V) and Cr(VI) although alternate oxidation states and metals may also be used. Such catalysts include manganese-based catalysts disclosed in U.S. Pat. Nos. 5,246,621, 5,244,594; 5,194,416; 5,114,606; and EP Nos. 549,271 A1, 549,272 A1, 544,440 A2, and 544,490 A1; preferred examples of these catalysts include $Mn^{IV}_2(\mu\text{-O})_3(TACN)_2\text{-}(PF_6)_2$, $Mn^{III}_2(\mu\text{-O})_1(\mu\text{-OAc})_2$ $(TACN)_2(ClO_4)_2$, $Mn^{IV}_4(\mu\text{-O})_6(TACN)_4(ClO)_4$, $Mn^{III}Mn^{IV}_4(\mu\text{-O})_1(\mu\text{-OAc})_2\text{-}(TACN)_2\text{-}(ClO_4)_3$, $Mn^{IV}\text{-}(TACN)-(OCH_3)_3(PF_6)$, and mixtures thereof wherein TACN is trimethyl-1,4,7-triazacyclononane or an equivalent macrocycle; though alternate metal-coordinating ligands as well as mononuclear complexes are also possible and monometallic as well as di- and polymetallic complexes and complexes of alternate metals such as iron or ruthenium are all within the present scope. Other metal-based bleach catalysts include those disclosed in U.S. Pat. Nos. 4,430,243 and U.S. Pat. 5,114,611. The use of manganese with various complex ligands to enhance bleaching is also reported in the following U.S. Pat. Nos.: 4,728,455; 5,284,944; 5,246,612; 5,256,779; 5,280,117; 5,274,147; 5,153,161; and 5,227,084.

Transition metals may be precomplexed or complexed in-situ with suitable donor ligands selected in function of the choice of metal, its oxidation state and the denticity of the ligands. Other complexes which may be included herein are those of U.S. application Ser. No. 08/210,186, filed Mar. 17, 1994. Other suitable transition metals in said transition-metal-containing bleach catalysts include iron, cobalt, ruthenium, rhodium, iridium, and copper.

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). NaSKS-6 can be prepared by methods such as those described in German DE-A-3,417,649 and DE-A-3,742,043. Other layered silicates, such as those having the general formula $NaMSi_xO_{2x+1}\cdot yH_2O$ wherein M is sodium or hydrogen, x is a number from 1.9 to 4, preferably 2, and y is a number from 0 to 20 can be used herein. Various other layered silicates from Hoechst include NaSKS-5, NaSKS-7 and NaSKS-11, as the alpha, beta and gamma forms.

Examples of carbonate builders are the alkaline earth and alkali metal carbonates as disclosed in German Patent Application No. 2,321,001 published on Nov. 15, 1973.

Aluminosilicate builders may be useful in the present invention. Aluminosilicate builders include those having the empirical formula:

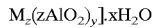

$$M_z(zAlO_2)_y]\cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

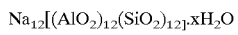

$$Na_{12}[(AlO_2)_{12}(SiO_2)_{12}]\cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of importance for liquid detergent formulations due to their availability from renewable resources and their biodegradability. Oxydisuccinates are also especially useful in such compositions and combinations.

Also suitable in the compositions of the present invention are the 3,3-dicarboxy-4-oxa-1,6-hexanedioates and the related compounds disclosed in U.S. Pat. No. 4,566,984, Bush, issued Jan. 28, 1986. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity.

Various alkali metal phosphates such as the well-known sodium tripolyphosphates, sodium pyrophosphate and sodium orthophosphate can be used. Phosphonate builders such as ethane-1-hydroxy-1-diphosphonate and other known phosphonates (see, for example, U.S. Pat. Nos. 3,159,58 1; 3,213,030; 3,422,021; 3,400,148 and 3,422,137) can also be used.

Enzymes—Suitable enzymes include proteases, amylases, lipases, cellulases, peroxidases, and mixtures thereof of any suitable origin, such as vegetable, animal, bacterial, fungal and yeast origin. Preferred selections are influenced by factors such as pH-activity and/or stability optima, thermostability, and stability to active bleach, detergents, builders and the like. In this respect bacterial or fungal enzymes are preferred, such as bacterial amylases and proteases, and fungal cellulases.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on surfaces such as dishware and the like. In practical terms for current commercial preparations, the compositions herein may comprise from 0.001% to 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

The preparation of protease enzyme and analogous enzymes is described in GB 1,243,784 to Novo. Other suitable proteases include ALCALASE® and SAVINASE® from Novo and MAXATASE® from International Bio-Synthetics, Inc., The Netherlands; as well as Protease A as disclosed in EP 130,756 A, Jan. 9, 1985 and Protease B as disclosed in EP 303,761 A, Apr. 28, 1987 and EP 130,756 A, Jan. 9, 1985. See also a high pH protease from Bacillus sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter & Gamble. When desired, a protease having decreased adsorption and increased hydrolysis is available as described in WO 9507791 to Procter & Gamble. A recombinant trypsin-like protease for detergents suitable herein is described in WO 9425583 to Novo.

Amylases suitable herein, especially for, but not limited to automatic dishwashing purposes, include, for example, α-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, Jun. 1985, pp 6518–6521 Preferred amylases include (a) an amylase according to the hereinbefore incorporated WO 9402597, Novo, Feb. 3, 1994. Other amylases include variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo.

Cellulases usable herein include those disclosed in U.S. Pat. No. 4,435,307, Barbesgoard et al, Mar. 6, 1984. Suitable cellulases are also disclosed in GB-A-2.075.028; GB-A-2.095.275 and DE-OS-2.247.832. CAREZYME® (Novo) is especially useful. See also WO 9117243 to Novo.

Suitable lipase enzymes for detergent usage include those produced by microorganisms of the Pseudomonas group, such as *Pseudomonas stuizeri* ATCC 530 19.154, as disclosed in GB 1,372,034. See also lipases in Japanese Patent Application 53,20487, laid open Feb. 24, 1978. Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. LIPOLASE® enzyme derived from *Humicola lanuginosa* and commercially available from Novo, see also EP 341,947, is a preferred lipase for use herein. Lipase and amylase variants stabilized against peroxidase enzymes are described in WO 9414951 A to Novo. See also WO 9205249 and RD 94359044.

Cutinase enzymes suitable for use herein are described in WO 8809367 A to Genencor.

Peroxidase enzymes may be used in combination with oxygen sources, e.g., percarbonate, perborate, hydrogen peroxide, etc., for "solution bleaching" or prevention of transfer of dyes or pigments removed from surfaces during the wash to other surfaces present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 to Novo and WO 8909813 A to Novo.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilized by various techniques. Enzyme stabilization techniques are disclosed and exemplified in U.S. Pat. No. 3,600,319, Aug. 17, 1971, Gedge et al, EP 199,405 and EP 200,586, Oct. 29, 1986, Venegas. Enzyme stabilization systems are also described, for example, in U.S. Pat. No. 3,519,570. A useful Bacillus, sp. AC13 giving proteases, xylanases and cellulases, is described in WO 9401532 A to Novo.

Enzyme Stabilizing System—Enzyme-containing, including but not limited to, liquid compositions, herein may comprise from about 0.001% to about 10%, preferably from about 0.005% to about 8%, most preferably from about 0.01% to about 6%, by weight of an enzyme stabilizing system. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition. See Severson, U.S. Pat. No. 4,537,706 for a review of Borate stabilizers.

Stabilizing systems may further comprise from 0 to about 10%, preferably from about 0.01% to about 6% by weight, of chlorine bleach scavengers, added to prevent chlorine bleach species present in many water supplies from attacking and inactivating the enzymes, especially under alkaline conditions. Suitable chlorine scavenger anions are widely known and readily available, and, if used, can be salts containing ammonium cations with sulfite, bisulfite, thiosulfite, thiosulfate, iodide, etc. Antioxidants such as carbamate, ascorbate, etc., organic amines such as ethylenediaminetetraacetic acid (EDTA) or alkali metal salt thereof, monoethanolamine (MEA), and mixtures thereof can likewise be used. Other conventional scavengers such as bisulfate, nitrate, chloride, sources of hydrogen peroxide such as sodium perborate tetrahydrate, sodium perborate monohydrate and sodium percarbonate, as well as phosphate, condensed phosphate, acetate, benzoate, citrate, formate, lactate, malate, tartrate, salicylate, etc., and mixtures thereof can be used if desired.

Material Care Agents—The present compositions may optionally contain as corrosion inhibitors and/or anti-tarnish aids one or more material care agents such as silicates. Material Care Agents are preferred especially in countries where electroplated nickel silver and sterling silver are common in domestic flatware, or hen aluminium protection is a concern and the composition is low in silicate. Material care agents include bismuth salts, transition metal salts such as those of manganese, certain types of paraffin, triazoles, pyrazoles, thiols, mercaptans, aluminium fatty acid salts, and mixtures thereof and are preferably incorporated at low levels, e.g., from about 0.01% to about 5% of the composition. A preferred paraffin oil is a predominantly branched aliphatic hydrocarbon comprising from about 20 to about 50, more preferably from about 25 to about 45, carbon atoms with a ratio of cyclic to noncyclic hydrocarbons of about 32 to 68 sold by Wintershall, Salzbergen, Germany as WINOG 70®. $Bi(NO_3)_3$ may be added. Other corrosion inhibitors are illustrated by benzotriazole, thiols including thionaphtol and thioanthranol, and finely divided aluminium fatty acid salts. All such materials will generally be used judiciously so as to avoid producing spots or films on glassware or compromising the bleaching action of the compositions. For this reason, it may be preferred to formulate without mercaptan antitarnishes which are quite strongly bleach-reactive or common fatty carboxylic acids which precipitate with calcium.

Chelating Agents—The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined.

Amino carboxylates usefull as optional chelating agents include ethylenediaminetetracetates, N-hydroxyethylethylenediaminetriacetates, nitrilotriacetates, ethylenediamine tetraproprionates, triethylenetetra-amine-hexacetates, diethylenetriaminepentaacetates, and ethanoldiglycines, alkali metal, ammonium, and substituted ammonium salts therein and mixtures therein.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene. A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Polymeric Dispersing Agents—Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Product/Instructions—This invention also encompasses the inclusion of instructions on the use of a product either on or in with the package or with other forms of advertising associated with the sale or use of the product. The instructions may be included in any manner typically used by consumer product manufacturing or supply companies. Examples include providing instructions on a label attached to the container holding the medical equipment; on a sheet either attached to the container or accompanying it when purchased; or in advertisements, demonstrations, and/or other written or oral instructions which may by connected to the purchase or use of a product containing a substrate and the treating composition.

Specifically the instructions will include a description of the use of the treating composition and microbe-containing medical equipment in connection with microwaving. The instructions, for instance, may additionally include information relating to the length of microwaving time; the recommended settings on the microwave; the recommended positioning of the medical equipment, container and the like, or whether soaking or rubbing is appropriate; the recommended amount of water, if any, to apply to the surface before and after treatment; other recommended treatment to accompany the microwave application.

Process—Methods for producing diacyl peroxide particles for use in the compositions herein wherein an abrasive particle is desired may include any particle making process commonly known in the art, including shear mixing. The diacyl particles for use herein can range in size from sub-micron (0.1) to about 100 microns. A preferred range is from about 1 to about 20 microns. Another process for making particles follows:

Process Description—The diacyl peroxide raw material particles are dissolved in an appropriate solvent (n-ethylpyrrolidone) and added to the rest of the formulation (primarily water, surfactant and thickener) with stirring. This procedure results in the in situ precipitation of the diacyl peroxide particles, resulting in a dispersion of small homogeneous particles ranging in size of from about 1 to about 20 microns. Optionally, commercially available diacyl peroxide raw material particles can be used which have particle sizes on the order of 800 microns or more, although these are not preferred.

Procedure for preparation of in situ particles: Laponite (33 g, 6% active) is dispersed in tap water (100 g) with stirring. Sodium Alkylethoxy sulfate (14 g, 70% active) is stirred into the Laponite dispersion and Sodium bicarbonate (1 g, 100% active) is added. In a separate container, Benzoyl peroxide (2 g, 75% active) is dissolved in N-ethylpyrrolidone (10 g, 100% active) with stirring. This benzoyl peroxide solution is then poured into the Laponite and surfactant solution with stirring. The mixture immediately turns cloudy and results in a homogeneous dispersion of 10–50 micron benzoyl peroxide particles.

In order to make the present invention more readily understood, reference is made to the following examples, which are intended to be illustrative only and not intended to be limiting in scope.

EXAMPLE

The following compositions are prepared for use as a treating composition. Each of the compositions are dispensed into "boat-shaped" containers, after which microbe-containing medical equipment is immersed in the compositions. The container containing the medical equipment and composition is then placed into a conventional household microwave and operated at the highest setting for the noted times, respectively.

| Ingredient | A | B | C |
|---|---|---|---|
| $C_{12-13}$ alkyl ether sulfate (avg. ethoxy of 1) | 3.0 | 3.0 | 2.0 |
| Magnesium chloride hexahydrate | 0.3 | 0.3 | — |
| Magnesium silicate[1] | 2.0 | 2.0 | 2.0 |
| Potassium bicarbonate | 1.0 | 1.0 | — |
| Acyl peroxide[2] | 2.0 | 2.0 | — |
| Perfume | 0.2 | 0.2 | — |
| Hydrogen peroxide | — | — | 3.0 |
| Mint flavor | 0.1 | 0.1 | 0.1 |
| Other (water, dye etc.) | to 100% | to 100% | to 100% |
| Microwave Time | 1 minute | 30 seconds | 2 minutes |
| Microbe removal (ASTM method) | 4-log reduction | 5-log reduction | 4-log reduction |

[1]Commercially available as Laponite RD®
[2]Acyl Peroxides selected from dibenzoyl peroxide, dianisoyl peroxide, benzoyl gluaryl peroxide, benzoyl succinyl peroxide, di-(2-methybenzoyl) peroxide, diphthaloyl peroxide, dinaphthoyl peroxide, substituted dinaphthoyl peroxide, and mixtures thereof.

All the medical equipment is then rinsed with fresh solvent such as water and allowed to dry, either by air or in a conventional oven. The percent microbe removal is determined by standard techniques (ASTM). As can be seen in this Example, all of the compositions A, B and C unexpectedly remove a sanitizing amount of microbes from the medical equipment in inexpensive and timely manner.

Having thus described the invention in detail, it will be clear to those skilled in the art that various changes may be made without departing from the scope of the invention and the invention is not to be considered limited to what is described in the specification.

What is claimed is:

1. A method for sanitizing medical equipment containing microbes, said method comprising the steps of:
   (a) contacting said medical equipment with an effective amount of a treating composition containing a surfactant and a solvent which generates heat under microwave radiation and a bleaching agent; and
   (b) subjecting said medical equipment and said treating composition to microwaves for an effective amount of time such that a sanitizing amount of said microbes are removed from said medical equipment, wherein the combination of the amount of the treating composition and the time of microwaving sterilizes said medical equipment.

2. A method according to claim 1 wherein said treating composition is aqueous.

3. A method according to claim 1 wherein said bleaching agent is selected from the group consisting of:
   a) diacyl peroxide;
   b) a source of hydrogen peroxide and bleach activator;
   c) a source of hydrogen peroxide;
   c) a chlorine bleach; and
   d) mixtures thereof.

4. A method according to claim 1 wherein said bleaching agent is a diacyl peroxide selected from the group consisting dibenzoyl peroxide, dianisoyl peroxide, benzoyl gluaryl peroxide, benzoyl succinyl peroxide, di-(2-methybenzoyl) peroxide, diphthaloyl peroxide, dinaphthoyl peroxide, substituted dinaphthoyl peroxide, and mixtures thereof.

5. A method according to claim 1 wherein said treating composition further comprises an ingredient selected from the group consisting of clay, polycarboxylate thickeners, baking soda, carbonates, phosphates, hydrobenzoic acid, dicarboxylic acid, siloxanes, perfumes, bleach catalysts, and mixtures thereof.

6. A method according to claim 1 wherein said solvent in said treating composition is water.

7. A method according to claim 1 wherein said effective amount of time is from about 30 seconds to about 5 minutes.

8. A method according to claim 1 wherein said effective amount of time is from about 30 seconds to about 3 minutes.

9. A method according to claim 1 wherein said sanitizing amount comprises removing at least about 50% of the microbes originally on said equipment.

10. A method according to claim 1 wherein said sanitizing amount comprises removing at least about 90% of the microbes originally on said equipment.

11. A method according to claim 1 wherein said sanitizing amount comprises removing at least about 99.9% of the microbes originally on said equipment.

12. A method according to claim 1 wherein said microwaves have an electromagnetic radiation wavelength of from about 1 cm to about 1 m.

13. A method according to claim 1 wherein said treating composition is a gel or liquid detergent composition comprising by weight:
   (a) from about 0.1% to about 60% of said bleaching agent which is selected from the group consisting of:
      i) diacyl peroxide having the general formula:

RC(O)OO(O)CR1 wherein R and R1 can be the same or different;
      ii) a source of hydrogen peroxide;
      iii) a source of hydrogen peroxide and a bleach activator;
      iv) a chlorine bleach; and
      v) mixtures thereof;
   (b) from 0% to about 95% of said solvent;
   (c) from 0.01% to about 50% of said surfactant; and
   (d) from 0% to about 7% of a thickener.

14. A method according to claim 1 wherein said treating composition is a gel detergent composition comprising by weight:
   (a) from about 0.1% to about 10% of a diacyl peroxide having the general formula:

RC(O)OO(O)CR1 wherein R and R1 can be the same or different;
   (b) from 0.01% to about 50% of said surfactant; and
   (c) from 0% to about 7% of a thickener;
      said composition having a neat pH of from about 3 to about 10; and such that said diacyl peroxide remains undissolved in said composition.

15. A method according to claim 1 wherein the treating composition is a liquid, and the step (a) comprises placing said medical equipment in a container containing said treat ing composition so that said medical equipment is at least partially immersed in said treating composition; and, said container with said medical equipment therein is placed into a microwave oven during step (b).

16. A method according to claim 15 wherein said surfactant creates a foam during step (b).

17. A method according to claim 16 wherein said medical equipment is substantially immersed in at least one of said liquid treating composition and said foam during step (b).

18. A medical equipment sanitizing product comprising:

a treating composition containing a surfactant and a solvent which generates heat under microwave radiation, and a bleaching agent; and instructions for using said treating composition, wherein said instructions describe the method of claim 1.

* * * * *